US010429457B2

(12) United States Patent
Haider et al.

(10) Patent No.: US 10,429,457 B2
(45) Date of Patent: Oct. 1, 2019

(54) MEDICAL IMAGING APPARATUS WITH OPTIMIZED OPERATION

(71) Applicant: Siemens Aktiengesellschaft, Munich (DE)

(72) Inventors: Sultan Haider, Erlangen (DE); Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 308 days.

(21) Appl. No.: 14/736,798

(22) Filed: Jun. 11, 2015

(65) Prior Publication Data

US 2015/0362566 A1  Dec. 17, 2015

(30) Foreign Application Priority Data

Jun. 11, 2014  (DE) .................... 10 2014 211 063

(51) Int. Cl.
*G01R 33/28* (2006.01)
*G01R 33/54* (2006.01)
*G16H 40/63* (2018.01)
*G01R 33/567* (2006.01)

(52) U.S. Cl.
CPC ......... *G01R 33/283* (2013.01); *G01R 33/288* (2013.01); *G01R 33/543* (2013.01); *G16H 40/63* (2018.01); *G01R 33/5673* (2013.01)

(58) Field of Classification Search
None
See application file for complete search history.

(56) References Cited

U.S. PATENT DOCUMENTS

| 4,831,645 A * | 5/1989 | Guenther | A61B 5/1077 378/205 |
| 6,175,610 B1 * | 1/2001 | Peter | A61B 6/00 250/221 |
| 6,317,619 B1 * | 11/2001 | Boernert | G01R 33/341 324/307 |
| 6,492,634 B2 * | 12/2002 | Marchitto | A61B 5/113 250/221 |
| 6,731,991 B1 * | 5/2004 | Michalski | G01B 11/24 353/18 |
| 2002/0151786 A1 * | 10/2002 | Shukla | A61B 5/055 600/411 |

(Continued)

FOREIGN PATENT DOCUMENTS

| CN | 102988069 A | 3/2013 |
| DE | 198 45 028 A1 | 6/2000 |
| DE | 10 2011 076 820 A1 | 12/2012 |

*Primary Examiner* — Katherine L Fernandez
*Assistant Examiner* — Yi-Shan Yang
(74) *Attorney, Agent, or Firm* — Schiff Hardin LLP

(57) ABSTRACT

In a method for operating a medical imaging apparatus in which an examination object is situated, information is detected indicating that at least one image of the examination object is to be created by the medical device. Next, a selection of an examination sequence is made from multiple stored, predefined examination sequences, and subsequently a detection occurs as to the step in the selected examination sequence at which the medical device is currently operating. Thereafter, a specification of the next step to be undertaken from the selected examination sequence is presented to a person operating the medical imaging apparatus.

11 Claims, 7 Drawing Sheets

(56) References Cited

U.S. PATENT DOCUMENTS

| | | | |
|---|---|---|---|
| 2005/0128184 A1* | 6/2005 | McGreevy | A61B 18/1206 345/156 |
| 2005/0195587 A1 | 9/2005 | Moctezuma De La Barrera et al. | |
| 2005/0261567 A1 | 11/2005 | Harder et al. | |
| 2006/0050930 A1* | 3/2006 | Szuba | A61B 5/4818 382/103 |
| 2006/0183997 A1* | 8/2006 | Haider | G01R 33/288 600/410 |
| 2006/0293588 A1* | 12/2006 | Beck | A61B 5/055 600/410 |
| 2007/0161871 A1 | 7/2007 | Haider et al. | |
| 2008/0071251 A1* | 3/2008 | Moubayed | A61M 5/172 604/890.1 |
| 2010/0312094 A1* | 12/2010 | Guttman | A61B 5/415 600/411 |
| 2011/0210734 A1* | 9/2011 | Darrow | G01R 33/543 324/309 |
| 2012/0010496 A1* | 1/2012 | Furudate | A61B 5/055 600/410 |
| 2012/0140068 A1* | 6/2012 | Monroe | H04N 7/183 348/143 |
| 2012/0189098 A1 | 7/2012 | Liu et al. | |
| 2013/0331664 A1* | 12/2013 | Gilad-Gilor | A61B 5/00 600/301 |
| 2013/0342350 A1 | 12/2013 | Popescu | |
| 2014/0149910 A1* | 5/2014 | Lee | A61B 6/465 715/771 |
| 2014/0241511 A1* | 8/2014 | Hausotte | A61B 6/08 378/206 |
| 2015/0087997 A1 | 3/2015 | Haider et al. | |
| 2015/0351709 A1* | 12/2015 | Dirauf | A61B 6/545 378/206 |
| 2015/0359464 A1* | 12/2015 | Olesen | A61B 5/721 600/476 |

\* cited by examiner

MEDICAL IMAGING APPARATUS WITH OPTIMIZED OPERATION

BACKGROUND OF THE INVENTION

Field of the Invention

The present invention relates to a method for operating a medical imaging apparatus and to a medical device for implementing such a method.

Description of the Prior Art

Medical imaging apparatuses, such as computed tomography (CTs) and magnetic resonance (MR) systems, for example, offer the user a very broad spectrum of options for creating images of an examination object, such as a person being examined. However the operation of such a medical device depends very heavily on whether experienced operators are present who are capable of operating such devices without errors. In the operation of MR systems in particular, different aspects have to be taken into account, such as the positioning of the RF coils, the support of the examination object on the table provided for this purpose, the selection of the correct imaging sequences etc.

Furthermore therapeutic measures or interventional applications are carried out in conjunction with imaging apparatuses, for example for removal of tissue or for performing minor operations. The doctor performing the operation can need further objects for this purpose. All these objects must be readily to hand in the correct location so that a smooth sequence of the examination can be insured.

The widespread use of these medical imaging apparatuses means that these devices are used in countries where, in addition to trained operating personnel, many inexperienced helpers assist in carrying out the examination sequence. Errors that occur can endanger the safety of the person being examined and furthermore endanger the smooth sequence which is necessary for the operation of these medical devices. Errors in operation can also lead to expensive repairs to the devices themselves.

U.S. Pat. No. 8,401,872 B describes a method as to how, based on a specific questionnaire, an imaging process can be optimized by omitting superfluous steps. However in this case the operator must know all the steps to be carried out in the examination sequence.

SUMMARY OF THE INVENTION

An object of the present invention is to further improve the operation of medical imaging apparatuses, especially to avoid errors during the operating sequence which could be harmful either to the medical device or to the person being examined.

In accordance with a first aspect of the invention, a method is provided for operating a medical imaging apparatus in which an examination object is examined. Information is detected automatically that at least one image of the examination object is to be created by the medical device. The medical device then selects an examination sequence from a number of stored, predefined examination sequences on the basis of the detected information. The predefined examination sequences each include a number of sequence steps. The step of the examination sequence in which the medical device is currently operating is also detected. The medical device automatically determines from this the next sequence step to be undertaken from the selected examination sequence and informs an operator of the device of the next step to be taken.

The fact that predefined examination sequences are stored and the medical device is capable of determining the sequence step in which the medical device is currently operating enables the operator to be informed about the next step to be taken. Errors in operation are thereby avoided, which improves the safety of the person being examined and through which possible damage to the medical device by usage errors are avoided. The information can be provided visually or acoustically or by audio-visual information.

The predefined examination sequences, as well as information which is necessary for the creation of the image (e.g. imaging parameters), also feature handling instructions as to how an operator is to act, which are to be carried out on the examination object, on the medical device or in an examination room in which the device is positioned.

Preferably the medical imaging apparatus has an illumination element in an examination room in which the medical device is positioned. For the next sequence step to be undertaken the medical device creates illumination information for the illumination element which is then displayed by the illumination element in the examination room. In many applications it is necessary for example for a further person to be present in the examination room, in order to position the person being examined or in the case of an interventional application, for carrying out an operation for example. Through the illumination information which is projected into the examination room, the operator in the examination room knows intuitively what to do next. Errors in usage are thus avoided.

For example the next step in the sequence can be the introduction of a couch with the examination object disposed on the couch. Here an illumination pattern can be determined for the illumination element, which is projected into the examination room in order to give the operator instructions as to how the couch must be positioned correctly at the medical device.

Furthermore the next sequence step can contain the determination of an examination region in the examination object. The illumination information created can be a grid which is projected onto the examination object. Subsequently the region is detected which is marked by the operator on the grid. This area is defined automatically as the examination area, wherein images are then created by the medical device in this examination area.

Furthermore the medical device can detect which objects are disposed in the examination room. The medical device can then check whether one of the detected objects of the objects detected in the examination room must be removed before the next step in the sequence is carried out. The operator is then informed optically or acoustically about the object to be removed before the next step in the sequence can be started.

Furthermore it can be determined from the detected objects that in the next step of the sequence one of these objects is necessary for carrying out the step in the sequence. The medical device can then detect where this object or the facility is located, wherein this object or this facility can be marked by the illumination element. Through this the operator knows which object is the next object that must be used. Furthermore the object to be used next can be shown on a display. Here as well, the operator is informed about which is the next step to be carried out, here the use of a specific object. The object to be used can for example be an RF coil, if the device is an MR system. The MR system can detect where the RF coils necessary for the examination sequence are arranged, for example with the use of sensors at predetermined locations at which the coils are to be placed or with the help of pattern recognition methods if images of the examination region are to be post-processed and objects identified, here for example the possible RF coils. The illumination element, in the knowledge of the position of the different RF coils, can then illuminate the RF coil which is the next to be connected to the MR system by the operator.

If the next step in the sequence is for example an interventional application on the person being examined, the operation devices present can be recognized by image recognition for example and once again the device or the facility which is to be the next one used for the next step in the sequence is optically marked.

The medical device can also compare the steps in the sequence carried out so far with the steps of the selected examination sequence. If an error is detected here the detected error can be displayed in order to possibly reverse the error or rectify it.

From the selected examination sequence the medical device can also determine how the examination object must be positioned on a couch. The illumination element can then project an optical silhouette onto the couch as to how the examination object must be positioned on the table for carrying out the examination sequence. This prevents an operator or a helper from positioning the person to be examined incorrectly on the couch. An example is whether the person being examined must be moved into the imaging apparatus head-first or feet-first.

Furthermore in the case of MR system, the system can deduce from the position of the examination object positioned on the couch, whether closed loops have been produced in the examination object. These closed loops can be a danger for the person being examined if induction currents form in the closed loops. The illumination element can then inform the operator, by illuminating the closed loop, that the positioning must be improved.

Furthermore hand movements of operators or persons being examined can be detected in the examination room and recognized, so that an operator in the examination room, through specific hand movements, can initiate specific processes at the medical device.

Furthermore the illumination element can mark the examination object and the marking on the examination object can be detected and evaluated by the medical apparatus, for example an image post-processing unit, in order to deduce breathing activity of the examination object from the movement of the marking for example.

The invention further relates to a medical imaging apparatus embodied as described above, with a detector unit for detection of the information that at least one image is to be created. Furthermore a sequence control is provided that detects the step in the sequence in which the medical device is currently operating and that determines the next step in the sequence to be undertaken, wherein this next step in the sequence is mapped on a display unit.

In addition to a camera for creation of images of the medical device and the environment in the examination room, the illumination element can be provided for creating the illumination information, as described above. As well as detectors for detection of the presence of MR coils for example, an image processing unit can post-process the images created and through object detection can detect objects, wherein the detected objects help in the removal of disruptive objects or in the identification of objects which can be needed for the next step in the sequence.

DESCRIPTION OF THE PREFERRED EMBODIMENTS

Using an MR system as an example of a medical imaging apparatus, it is explained below how errors in an examination sequence can be prevented, wherein it is insured that neither the person being examined nor the medical device itself is damaged. Although the description below refers to an MR system, the invention can also be used for other medical imaging apparatuses, such as a CT or other imaging facilities, for example.

Figure 1:
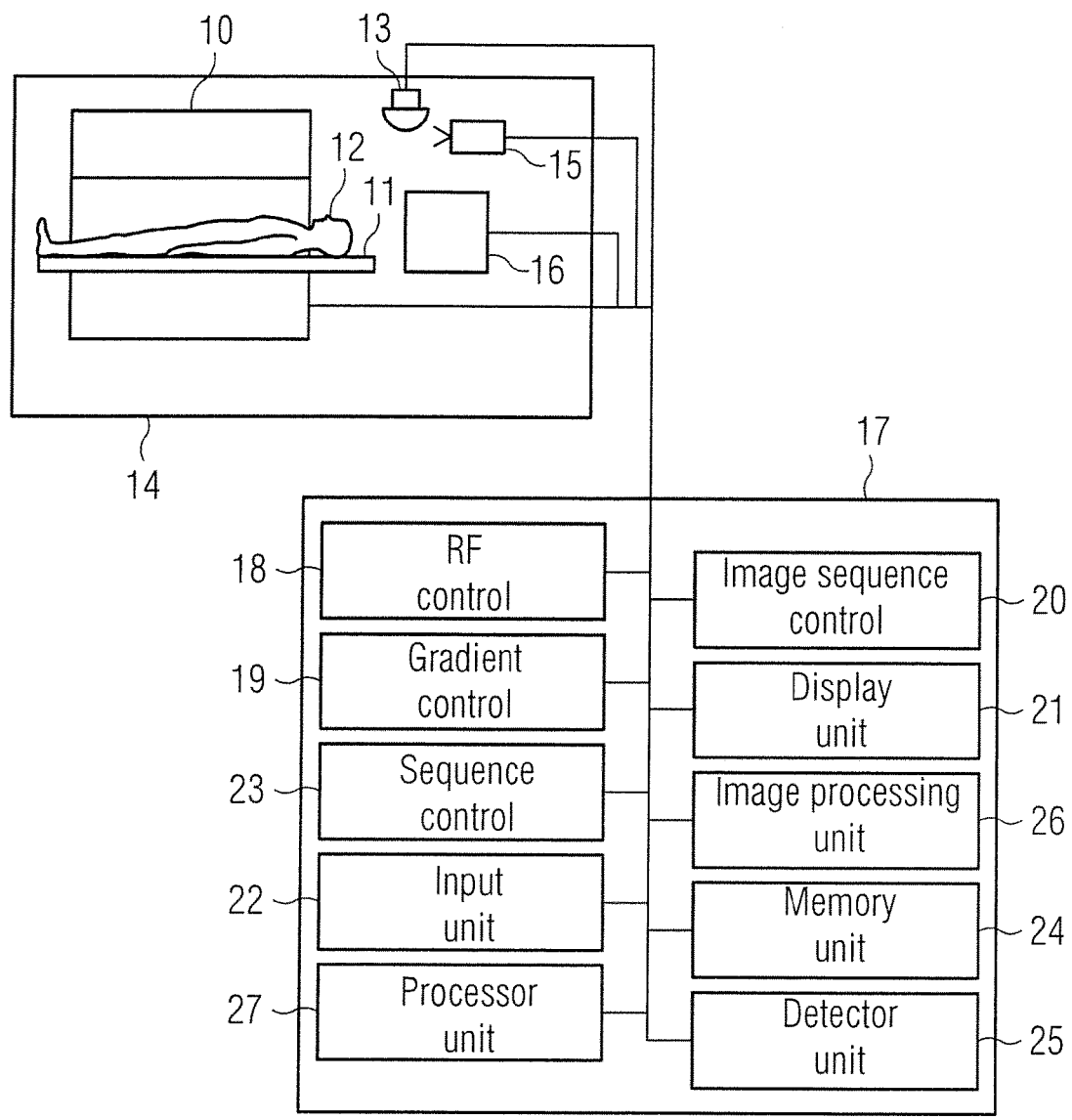
FIG. 1 schematically shows an MR system as a medical imaging apparatus with which, in accordance with the invention, an examination sequence can be carried out without errors and at no risk.

The MR system shown in FIG. 1 has a scanner with a magnet 10 for creating a polarization field B0. A person being examined 12 disposed on a bed 11 is moved into the MR system, wherein, in the magnet 10, a magnetization of nuclear spins produced in the person 12 is deflected or spatially-coded by the RF pulses and magnetic field gradients. The MR signals produced can be detected by MR coils not shown in the FIG. 1. How MR images of a person being examined are created by applying RF pulses and switching the magnetic field gradients is known to those skilled in the art and thus need not be explained further in detail herein.

The MR system also has an illumination unit 13 which, as explained later, can help an operator in an examination room 14 in which the MR system is disposed in carrying out steps in a sequence. A camera 15 creates images from the examination room. The images created by this camera 15 can serve as a basis for recognition of objects in the examination room 14. Information either for the person being examined or the operator can be displayed on a display unit 16. The information presented on the display unit 16 can have been created directly for the display unit 16, wherein an image is created there in the display unit, or the illumination unit can be embodied so that it has a projection unit, which projects the created information onto the display unit 16. This MR system also has a central control computer 17. An RF control 18 controls the creation of the RF pulses which are radiated into the person being examined 12, a gradient control 19 controls the switching of the magnetic field gradients for local encoding of the signals. After selection of an imaging sequence, an image sequence control 20 controls the temporal order of the RF pulses and of the magnetic field gradients and thus likewise controls the RF control 18 and the gradient control 19. Information can be displayed on a display unit 21 for an operator outside the examination room 14 such as the created MR images for example. An operator can enter information via the input unit 22 and control the functioning of the MR system.

The MR system likewise has a sequence controller 23. This sequence controller 23 controls the examination sequence, as will be further explained in detail below, such that the MR system can be operated without errors. In particular, the sequence controller 23 either itself evaluates operating parameters of the MR system, or uses a detector unit 25, to determine the state of an examination sequence in which the MR system is currently operating. The MR system also has a memory 24 in which, inter alia, a number of pre-defined examination sequences can be stored. In such examination sequences it is precisely defined for different anatomical regions which steps must be carried out to create the MR images. These examination sequences not only feature, as was previously usual, the different imaging sequences which must be measured in a specific anatomical region, but the examination sequences also have steps which an operator that the MR system must carry out in order to carry out the next step, for example the positioning of the person being examined on the couch 11, the selection of the RF coils for irradiating radiating and/or detecting the MR signals or other steps which an operator at the MR system must carry out, for example which facilities must be used when in an operation.

On the basis of the detected information as to the operating state that the MR system is currently in, and on the basis of the information as to what must be implemented in order to obtain images with the medical device, the sequence controller 23 selects one of the predefined examination sequences. For example, an operator can specify that MR images of a specific anatomical area are to be created. On the basis of the anatomical area, the associated sequence protocol is determined. With the selected examination sequence and the current operating state, the MR system or sequence controller 23 can then identify the next step to be carried out and create information for the operator, for example with the use of the display unit 16 or with the use of the illumination element 13. Preferably the information needed is displayed within the examination room 14.

An image processing unit 26 can post-process the images created by the camera 15 and, by detecting predefined patterns within the images, can recognize objects. These recognized objects can for example be illuminated by the illumination element 13, through which an operator is informed as to the next object needed within the examination room.

The sequences of the MR system can be controlled with a processor unit 27 having one or more processors. The processor unit 27 can especially be controlled by program commands from computer programs which are stored, for example, in the memory unit 24. The MR system can of course have further functional units not shown in the figure. Furthermore the units shown do not have to be implemented with the separation shown. The functional units shown can also be realized in fewer physical units, and multiple units can be combined in a single unit.

Figure 2:
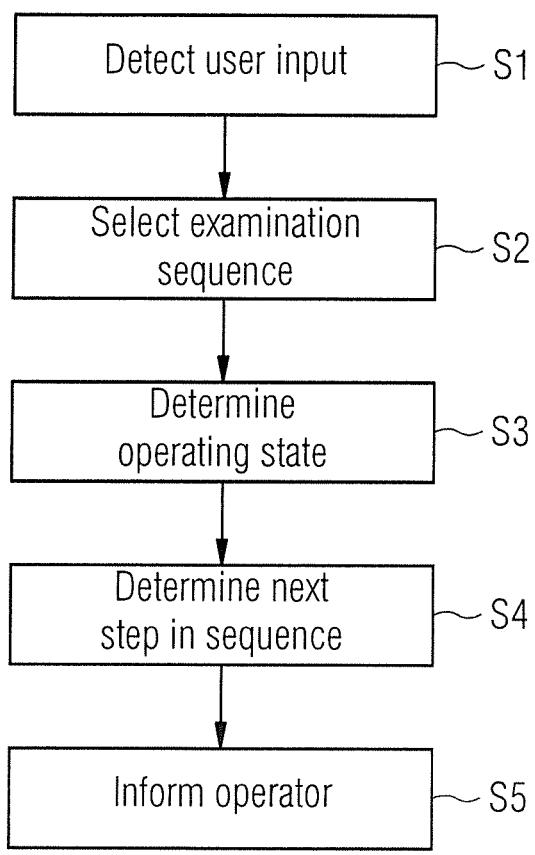
FIG. 2 is a flowchart of the basic steps for carrying out the method, with which errors in the recording of images can be avoided.

FIG. 2 schematically illustrates operating or functional steps with which the MR system of FIG. 1 can optimize an examination sequence. In a first step S1, an input made by a user of the MR system can be detected for example, wherein the user enters via the input unit 22 (interface), for example, that MR images of the head or MR images of the abdomen of a person being examined are to be recorded. With the use of this information it is possible for the MR system to select from the predefined examination sequences an examination sequence with which the requirements entered in step S1 can be carried out. The information detected in step S1 does not necessarily have to be present before the beginning of an MR examination. It is also possible for the person being examined to already be lying in the MR system and then for a user of the MR system, especially a user of the central control unit 17, to enter information that now a specific problem is to be examined, such as for example that an interventional application is started or for example that contrast medium should start to be administered to the person being examined.

After the selection of a suitable examination sequence in step S2 by the MR system, a check is made in step S3 as to which operating state the MR system is currently in, i.e. at which step of the selected examination sequence. With this information determined in step S3, the next step in the sequence, which must now follow, can be determined in step S4. In step S5 the operator can then be informed about the next step in the sequence.

In general the selected examination sequence and the predefined examination sequences, in addition to information about the image to be created, also feature instructions to an operator of the medical device which the operator must carry out manually at the MR system, especially in the examination room.

Different situations are explained below in which information as to which is the next step to be carried out is given to an operator mostly via visual illumination information or an illumination pattern. The user named in FIG. 2 in step S1 can be the person who is controlling the MR system or the medical device at the central control unit 17. This user is usually situated outside of the examination room. An operator below is a person who is situated in the examination room and who must carry out manual actions therein for the examination sequence. The user of step S1 and the operator of step S5 can be the same person, or can be different people.

Figure 3:
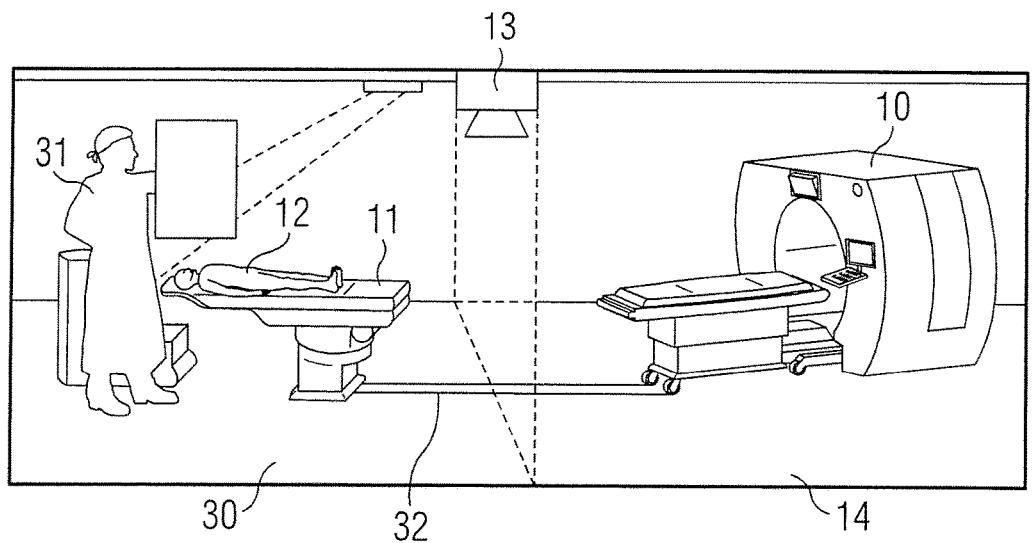
FIG. 3 shows a typical embodiment as to how, by creating an illumination pattern, the sequence of the method can be improved during imaging.

FIG. 3 shows schematically how an operator is supported in such cases in correctly positioning a couch 11 on which the person being examined 12 is disposed at the magnet 10. For this an illumination pattern 32 can be projected by the illumination element on the floor 30 of the examination room 14 which displays to an operator 31 how the couch must be moved so that the couch is positioned correctly in the MR system, so that the person being examined 12 can be moved into the MR system.

Figure 4:
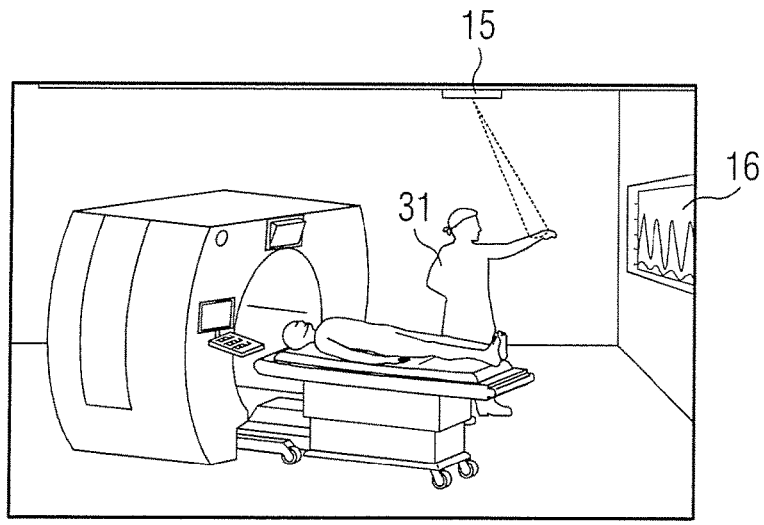
FIG. 4 shows an embodiment as to how the examination can be optimized by display of information.

FIG. 4 shows an example of how, with the use of the camera 15, images of the examination room can be created, especially by the operator 31, with gestures performed by the operator 31 being recognized in the image processing unit 26. Information can be displayed on the display unit 16 for example about how the imaging sequence is to be used, the created MR images, a breathing or heart signal of the person being examined or any other information. By moving his or her hand, the operator 31 can control the execution sequence of the MR system, for example objects displayed on the display unit 16 can be selected or by any other predefined operations, such as a wipe movement or predefined pattern, the operator can issue commands which can be recognized by the image processing unit 26 and can be converted into working steps.

Figure 5:
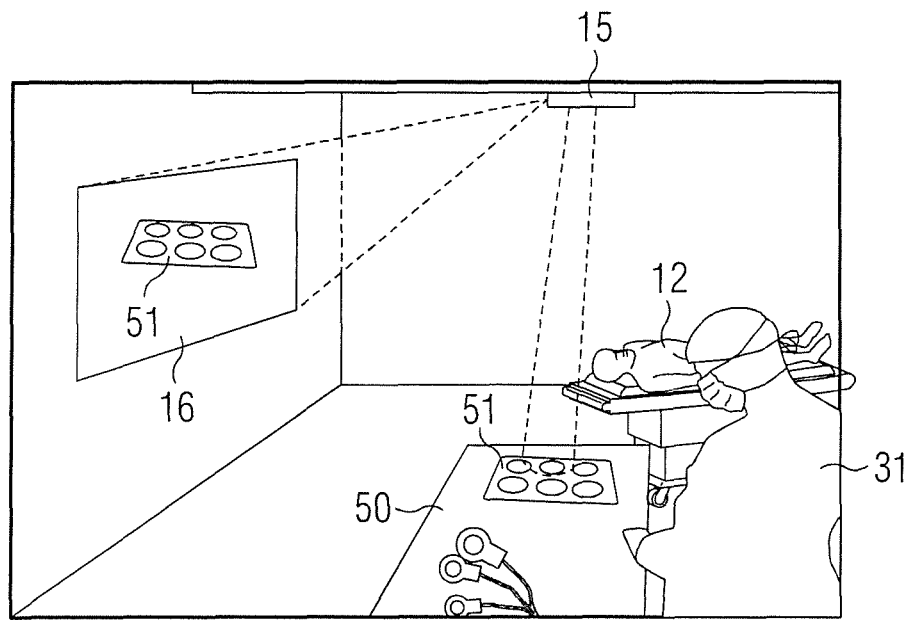
FIG. 5 shows an embodiment in which an operator is shown which RF coil is to be used in the examination.

FIG. 5 shows how the operator 31 is informed about which RF transmit or receive coil is to be used during an examination sequence. If the MR system knows, after the selection of the examination sequence in step S2 of FIG. 2, which examination steps are to be carried out, the camera 15, for example, can project onto the display unit 16 or onto a surface 50, the RF coil 51 that is to be selected by the operator 31, and that is to be placed on the person being examined.

Furthermore, it is possible that there are predefined locations available for placing the different coils. These locations can be equipped with sensors, which detect whether the coils are in place in each case. Furthermore, there is the option of detecting through the images created by the camera 15 and by image post-processing whether the various RF coils are in the place intended for them. The illumination element not shown in FIG. 5 can then subsequently, if the position of the coil has been detected in the examination room, illuminate this coil, so that the operator knows that this coil is the next to be positioned at the MR system. The illumination element can additionally mark the position on the MR system at which the coil is to be fastened.

Figure 6:
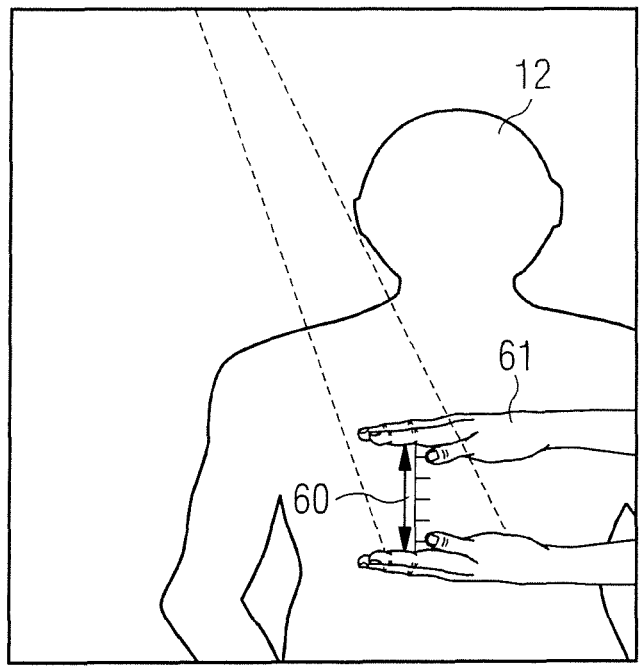
FIG. 6 shows an example of how the examination region can be defined in a simple manner for a person being examined.

FIG. 6 shows an example of how illumination information created by the illumination element represents a grid that is displayed on the person being examined 12. For example a line with graduations can be projected onto the person being examined 12. An operator can then define the examination area, such as the examination area 60 in which the MR images are to be created, manually by displaying grid points. The position of the hand 61 can be detected by the camera and the image post-processing unit can determine how the examination area 60 is defined. This information can be transmitted to a control of the couch 11 for example, e.g. the sequence control, which then positions the person being examined 12 in the MR system so that the examination area 60 lies in the center of the magnet 10.

Figure 7:
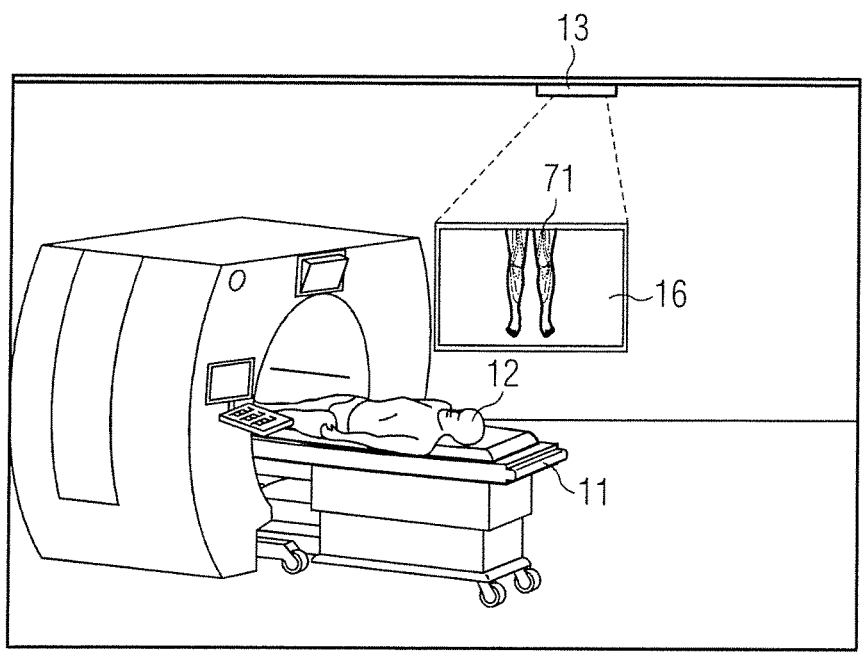
FIG. 7 shows an example of a display presentation that makes it possible for an operator to position the person being examined correctly in the MR system.

FIG. 7 shows how the MR image which was just measured, created by the MR system, is displayed on the display unit in the examination room 14. In another form of embodiment the operating information displayed on the display unit can also serve to position the person being examined 12 correctly in the MR system. The feet 71 shown on the display unit 16 can help the operator in positioning the person being examined in the MR system, for example. Through the displayed information, the operator can know, for example, that the person being examined 12 is to be moved feet-first into the MR system. Furthermore it is possible for the illumination element 13 to show a silhouette on the bed 11, from which the operator can deduce how the person being examined is to be laid on the bed, with feet first or with head first.

Figure 8:
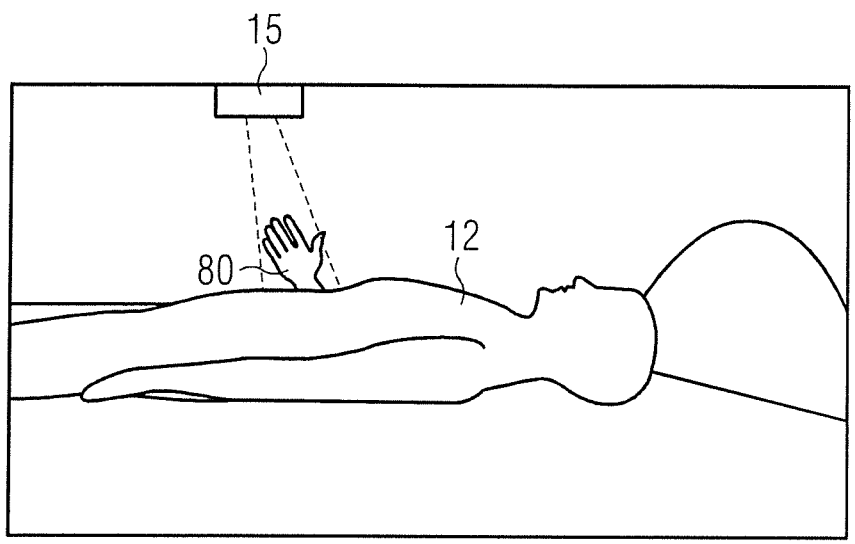
FIG. 8 schematically shows how the wishes of the person being examined can be detected by gesture recognition.

FIG. 8 shows how the person being examined 12 makes a specific gesture with their hand 80, which is detected by the camera 15 and is processed in the image post-processing unit 26. For example, a specific hand gesture can mean that the person being examined would very much like to actuate the emergency button, which immediately aborts the examination sequence.

Figure 9:
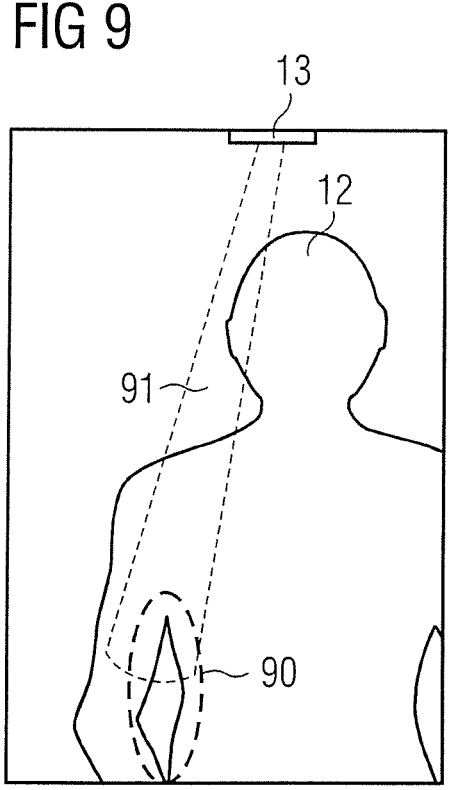
FIG. 9 shows an example of how the occurrence of loops in a person being examined can be marked by an illumination element.

FIG. 9 shows how it is established by the camera 15 and the image processing unit 26 that the person being examined 12 is positioned in the MR system so that an undesired loop 90 is produced. These loops can occur when extremities move at their end or touch other areas of the body. In these loops induction currents can form which can lead to injuries to the person being examined 12. The illumination element 13 can mark the information about the detected loop 90 via a light beam 91 so that, in addition to visual information on the display unit 21, an operator knows immediately where the loop has formed.

Figure 10:
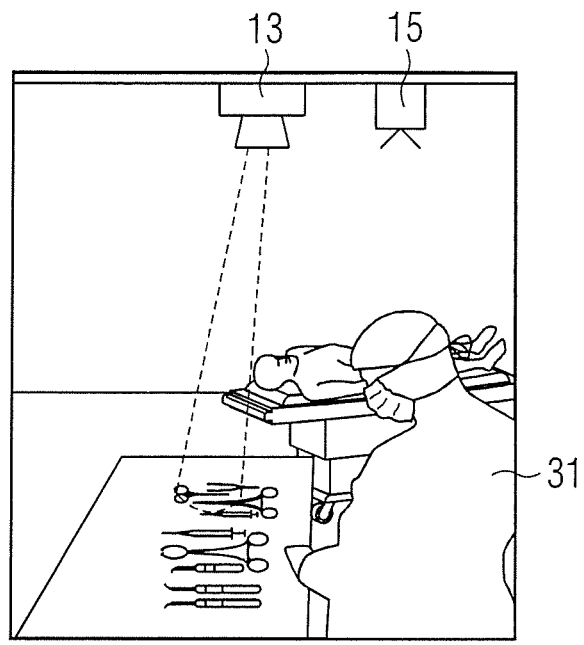
FIG. 10 shows an example of how an operator is informed as to which is the next object to be used in an examination sequence.

FIG. 10 shows how, with an operative application within the examination room, objects that are needed by the operator 31, for example for performing a specific operation, are identified by images taken by the camera 15. If the next step in the sequence to be performed of the selected examination sequence contains the information that a predetermined object is now to be used, such as a predetermined surgical tool or another object, the object can be illuminated, then after being recognized by the image processing unit 26, the object can be illuminated by the illumination element 13 so that the operator knows which object or which instrument should be selected next.

Figure 11:
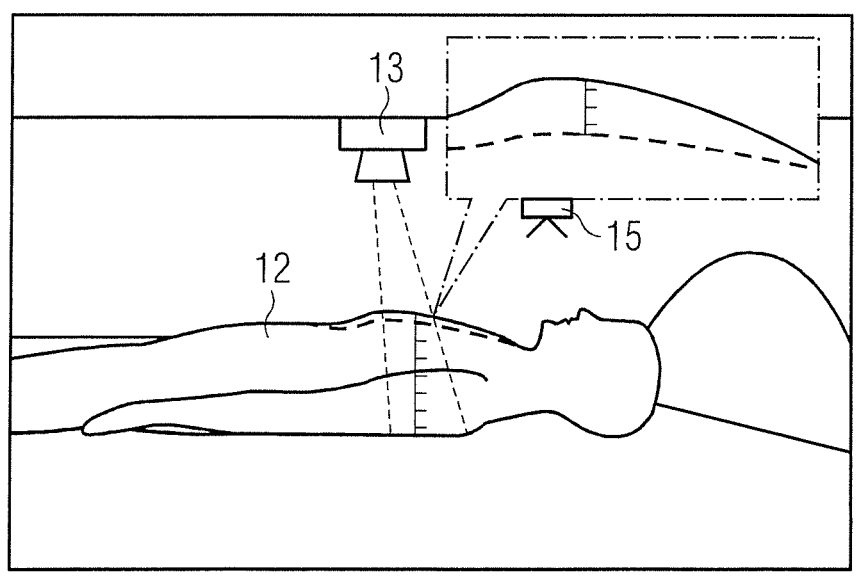
FIG. 11 schematically shows how, by illumination of the person being examined, breathing movement of the person can be detected.

FIG. 11 shows how breathing movement of the person being examined 12 can be detected. If, for example, the thorax of the person being examined is illuminated by the illumination element 13 and this information is detected by the camera 15, movement of the surface of the thorax indicates how breathing movement is occurring.

In summary the sequence control provides information as to what is to be done in which step, and which activity is to be performed, by the operator. As well as the examples presented in the figures, it can be detected by the images, for example, whether an undesired object is located in the examination room 14. If no person is to be in the examination room 14 during the examination, then these persons can be recognized in the images taken by the camera. A user of the MR system can be informed that unauthorized persons have still been detected in the examination room and that it is not possible to continue the sequence. Furthermore a checklist can be displayed on the display unit, with the aid of which the operator can check whether all preparatory steps have been carried out before the next sequence step. The display unit 16 can also be used after the start of the examination for distracting and entertaining the person being examined or the display unit can be used for presenting optical stimulations, as are needed, for example, with functional MRI measurements (fMRI). The display unit can be attached to a wall, to the sealing of the examination room or also on a table or another element of the MR system. The camera can detect which RF coil is being used in the RF system and can compare this coil with the information which is stored in the examination sequence. If there is no match, the operator can be informed about the incorrect choice of coil. The camera can likewise estimate the size and the weight from a recording of the person being examined by image post-processing and this information can be used for the input of information about the person being examined. The illumination element can also mark an area on the person being examined, which specifies where an examination should take place in the body. For this, after recognition of the outline of the body by the camera, the area of which an examination is to be made is marked by light.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a medical imaging system that is situated in an examination room, said method comprising:

providing detected information to a control processor of the medical imaging system, after detecting that image data of a patient are to be acquired by operation of the medical imaging system;
  in said control processor, selecting an examination sequence, as a selected examination sequence that is dependent on the detected information, from among a plurality of stored predetermined examination sequences, wherein
    each of said plurality of stored predetermined examination sequences comprising a plurality of predetermined examination steps consisting of a first category of steps that are to be performed by said medical imaging system and a second category of steps that involve a manual action that is to be performed by an operator of the medical imaging system on an object other than said control processor that is in said examination room;
  generating control signals for said first category of steps and emitting said control signals to the medical imaging system in order to operate the medical imaging system so as to execute said selected examination sequence;
  in said control processor, after beginning execution of the selected examination sequence, when the selected examination sequence is ongoing, detecting a current examination step in the ongoing selected examination sequence in which the medical imaging system is currently operating;
  in said control processor, consulting said ongoing selected examination sequence in order to identify that a next predetermined step in the ongoing selected examination sequence is in said second category of steps, said next predetermined step being required by said ongoing selected examination sequence to immediately follow the detected current examination step in the ongoing selected examination sequence;
  in said control processor, when it is determined that said next predetermined step is in said second category of steps, generating step information that represents said manual action to be performed in said next predetermined step; and
  in said control processor, generating projector control signals from said step information and emitting said projector control signals from said control processor to an image projector in order to operate said image projector so as to project an image, corresponding to said step information, on a projection surface to inform said operator of the manual action that must be performed in said next predetermined step.

2. A method as claimed in claim 1
wherein said medical imaging system comprises, as said object, a bed on which the patient is situated,
wherein said next predetermined step comprises, as said manual action, moving said bed, with the patient thereon, to the medical imaging system, and
wherein said step information is an illumination pattern in said image designating how the bed must be correctly positioned with respect to said medical imaging system.

3. A method as claimed in claim 2
wherein said next predetermined step requires determination of an examination area of the patient as said object,
wherein said step information comprises a grid that is projected in said image onto the patient on the bed as said projection surface, and
wherein said manual action comprises manually marking a marked area on the patient using said grid, said marked area corresponding to said examination area.

4. A method as claimed in claim 1 further comprising
identifying steps in said first category, as executed steps, that have already been executed by said medical imaging system prior to said detected current examination step,
comparing the executed steps to said predetermined steps in said ongoing selected examination sequence that precede said detected current examination step, and
emitting an error message from said control processor if the executed steps do not match the predetermined steps in the ongoing selected examination sequence that precede said detected current examination step.

5. A method as claimed in claim 1
wherein said medical imaging system is a magnetic resonance imaging system comprising, as said object, at least one radio-frequency (RF) coil among multiple different RF coils, and further comprising,
in said control processor, determining which RF coil, among said multiple different RF coils, is needed to execute said next predetermined step;
generating said step information so as to designate said RF coil needed to execute said next predetermined step; and
operating said image projector so as to include, in said image, a designation of said RF coil needed to execute said next predetermined step, and to designate said manual action as selecting said RF coil needed to execute said next step from among said multiple RF coils.

6. A method as claimed in claim 1
wherein said medical imaging system is a magnetic resonance imaging system,
wherein said method further comprises
  detecting, as said object, an occurrence of a closed inductance loop in the patient at a location occupied by the patient in the magnetic resonance imaging system and, if the occurrence of said closed loop is detected;
  generating said step information so as to include a designation of said closed induction loop; and
  projecting said image to provide an optical identification of said closed induction bop at said location occupied by the patient in the medical imaging system, and
wherein said manual action comprises adjusting said patient to open said closed induction loop.

7. A method as claimed in claim 1
wherein said medical imaging system comprises a bed, as said object, on which the patient is situated in the medical imaging system, and
wherein said method comprises
  generating said step information so as to include a designation of how the patient must be positioned on said bed in order to execute the next predetermined step, and
  projecting in said image an optical silhouette onto the bed, as said projection surface, that designates how the examination object must be positioned on the bed, as said manual action, in order to execute the next predetermined step.

8. A method as claimed in claim 1 further comprising
detecting a hand movement of the operator and, in said processor, determining a command, from the detected hand movement, for one of said steps in said first category and thereafter executing said command by said medical imaging system.

9. A medical imaging apparatus comprising:
a medical imaging system that is situated in an examination room,
an image projector, and
a control processor configured to detect information that image data of a patient are to be generated by operation of the medical imaging system wherein
said control processor being configured to select an examination sequence, as a selected examination sequence that is dependent on the detected information, from among a plurality of stored predetermined examination sequences, each of said plurality of stored predetermined examination sequences comprising a plurality of predetermined examination steps consisting of a first category of steps that are to be performed by said medical imaging system and a second category of steps that involve a manual action to be performed by an operator of the medical imaging system on an object in the examination room;
said control processor being configured to generate control signals for said steps in said first category and to emit said control signals to the medical imaging system in order to operate the medical imaging system so as to execute said examination sequence;
said control processor being configured to detect, after beginning execution of said selected examination sequence when the selected examination sequence is ongoing, a current examination step in the ongoing selected examination sequence in which the medical imaging system is currently operating;
said control processor being configured to consult said ongoing selected examination sequence in order to identify whether a next predetermined step in the ongoing selected examination sequence is in said second category steps, said next predetermined step being required by said ongoing selected examination sequence to immediately follow the detected current examination step in the selected examination sequence; said control processor, when it is determined that said next predetermined step is of in said second category of steps, being configured to generate step information that represents said manual action in said next predetermined step; and
said control processor being configured to generate projector control signals from said step information and to emit said projector control signals from said control processor to said image projector in order to operate said image projector so as to project an image, corresponding to said step information, on a projection surface in order to inform said operator of the manual action that must be performed in said next predetermined step.

10. A medical imaging apparatus as claimed in claim 9, further comprising:
a camera that obtains a camera image of said examination room including a plurality of examination room objects that are situated in said examination room;
an image processor in communication with said camera that applies a pattern recognition algorithm to said camera image in order to identify, among said plurality of examination room objects, said object that involves said manual action that is to be performed by said operator, as an identified object; and
said control processor is further configured to receive a designation of said identified object from said image processor and to include, in said image, a representation of said identified object.

11. A method as claimed in claim 7 comprising:
using a camera to obtain a camera image of said examination room including a plurality of examination room objects that are situated in said examination room;
in an image processor in communication with said camera, applying a pattern recognition algorithm to said camera image in order to identify, among said plurality of examination room objects, said object that involves said manual action that is to be performed by said operator, as an identified object; and
providing said control processor with a designation of said identified object from said image processor, and
in said control processor, including, in said image, a representation of said identified object.

\* \* \* \* \*